United States Patent [19]

Venturello et al.

[11] 4,242,524
[45] Dec. 30, 1980

[54] PROCESS FOR THE PREPARATION OF 2-(4'-NITROPHENYL)-PROPIONIC ACID

[75] Inventors: Carlo Venturello, Turin; Rino D'Aloisio, Novara; Aldo Belli, Intra, all of Italy

[73] Assignee: Montedison S.p.A., Milan, Italy

[21] Appl. No.: 31,916

[22] Filed: Apr. 20, 1979

Related U.S. Application Data

[63] Continuation of Ser. No. 894,346, Apr. 7, 1978.

[30] Foreign Application Priority Data

Feb. 9, 1978 [IT] Italy ................. 20095 A/78

[51] Int. Cl.³ ............................................. C07C 51/15
[52] U.S. Cl. ..................................................... 562/423
[58] Field of Search ......................................... 562/423

[56] References Cited

U.S. PATENT DOCUMENTS

| | | | |
|---|---|---|---|
| 3,557,196 | 1/1971 | Bottaccio | 562/423 |
| 3,734,955 | 5/1973 | Patmore | 562/423 |
| 3,976,677 | 8/1976 | Bottaccio | 562/423 |

OTHER PUBLICATIONS

Bielstein, Band IX, p. 526.
Bielstein, Band IX (I), p. 207.

*Primary Examiner*—Paul J. Killos
*Attorney, Agent, or Firm*—Morgan, Finnegan, Pine, Foley & Lee

[57] ABSTRACT

The present invention concerns a process for the preparation of 2-(4'-nitrophenyl)-propionic acid of the formula (I):

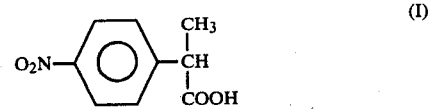

More particularly, this invention relates to a process for the preparation of 2-(4'-nitrophenyl)-propionic acid (I) starting from para-nitroethylbenzene (PNEB) by carboxylation in the presence of alkaline phenates (Na and K).

The 2-(4'-nitrophenyl)-propionic acid (I) thus obtained finds a useful application as an intermediate for the preparation of chemical products.

For instance, acid (I) may be hydrogenated catalytically until obtaining the corresponding amino-derivative which is then condensed with ortho-cyanobenzyl-bromides in order to give isoindoline (as described in Belgian Pat. No. 774985).

6 Claims, No Drawings

PROCESS FOR THE PREPARATION OF 2-(4'-NITROPHENYL)-PROPIONIC ACID

This is a continuation of application Ser. No. 894,346, filed Apr. 7, 1978.

BACKGROUND OF THE INVENTION

It is known to prepare 2-(4'-nitrophenyl)-propionic (I) acid by nitration of 2-phenyl-propionic acid or of the corresponding nitrile and by successive saponification.

However, these techniques show drawbacks due to the difficulty to supply the starting products and, especially also to the necessity to separate the nitration isomer products, an operation of not easy industrial realization.

Equally known is the carboxylation with $CO_2$ of the para-nitroethylbenzene in dimethylformamide (DMF) in the presence of alkaline phenates. Nevertheless, this process, although offering some advantages from the point of view of the selectivity, yield and operational simplicity in comparison with the previously cited alternative processes, is not free from a number of drawbacks. In fact, the carboxylation reaction in DMF, besides the desired monocarboxylic (I) product, leads to consistent quantities, depending on the parametric conditions used, of the dicarboxylated product (paranitrophenylmethyl-malonic acid) better defined later on, with the introduction of a second-COOH group on the same carbon atom carrying the first group. This drawback makes it necessary to introduce a decarboxylation stage in order to eliminate the unwanted —COOH group, an operation that is, at any rate, possible according to known methods.

Moreover, the DMF solvent used is unstable under prolonged and/or repeated heating in an alkaline medium and, thus, the alkaline phenate necessary for the reaction, and which at the end of that reaction will be found in the form phenol, cannot be formed again in the presence of DMF which must thus be preliminarily separated.

In other words, the alkaline phenate must be prepared separately involving operational and economical problems of a certain purport. On the other hand, the actual possibilities of separation and recovery of the DMF from the phenol of the aqueous solutions at the end of the reaction, are practically inconsistent because of the great difficulties met in the extraction with solvents of the DMF from aqueous solutions. In fact, under those conditions only part of the DMF that is associated somehow with phenol is extracted, wherefore this latter cannot be in its turn used again.

Such difficulties bring with them the necessity of disposing and/or destroying great quantities of DMF solvent and phenol, with heavy economical and environmental implications.

Thus, an object of this invention is that of providing a process that is operationally accessible and economically convenient for the preparation of the 2-(4'-nitrophenyl)-propionic (I) acid.

GENERAL DESCRIPTION OF THE INVENTION

This and still other objects that will appear more clearly to the skilled in the art from the description that follows, are achieved, according to this invention, by a process for the preparation of 2-(4'-nitrophenyl)-propionic (I) acid, by carboxylation of the para-nitro-ethylbenzene in a solvent, under substantially atmospheric pressure, and at a temperature comprised between about 20° and 50° C., in the presence of alkaline phenates (Na and K), characterized in that the reaction is conducted in dimethylsulphoxide (DMSO) as a solvent, preferably in the presence of paracresolate of potassium. The acid (I) is obtained from the corresponding alkaline salt thus prepared, using standard techniques for salt to acid conversion.

The reaction may be diagrammatically represented by the following equation (1):

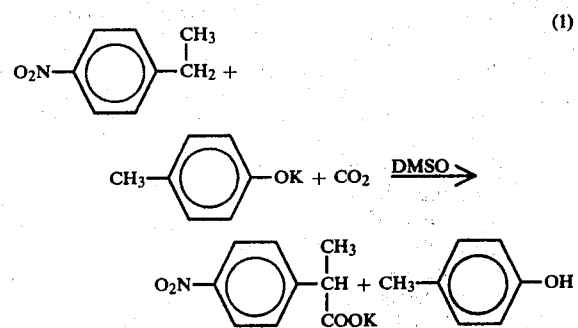

According to a further unexpected characteristic of this invention, not deducible from the prior art, the possible dicarboxylation product already cited and obtained according to the secondary reaction (2):

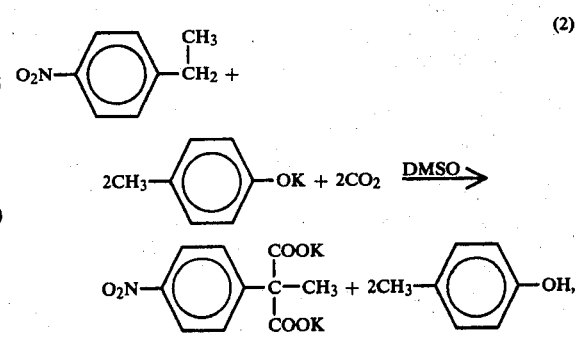

in the successive treatment with a mineral acid (HCl, $H_3PO_4$), in order to obtain the acid from the alkaline salt, directly decarboxylates to the corresponding desired monocarboxylic (I) acid.

Summing up, the process may be represented in its whole by the following equation (3):

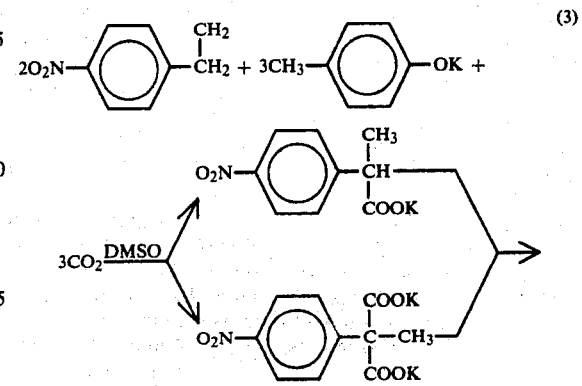

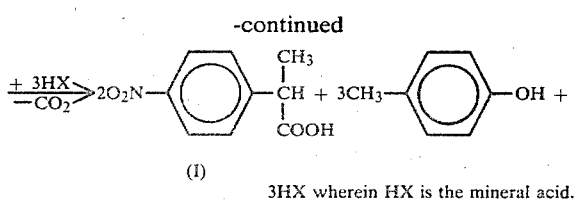

(I)     3HX wherein HX is the mineral acid.

The process is conducted in dimethylsulphoxide. Alternatively, it is possible to use also pyridine, 3-picoline or mixtures thereof with DMSO.

The molar ratio phenate/PNEB may vary within a very wide range, but preferably is comprised between 1 and 4.

As an alkaline phenate there may be used potassium paracresolate. The temperature is usually maintained at between 20° and about 50° C.

The process of this invention is especially characterized, thus, in that DMSO is used as the solvent associated with potassium para-cresolate as the alkaline phenate, at the end of the carboxylation reaction of equation (3) thereby obtaining a mixture consisting predominantly of the alkaline (potassic) salt of acid (I), in the presence of lesser quantities of the alkaline salt of the bicarboxylic acid. The latter in the successive acidulation is decarboxylated to (I).

Thus, in the reaction mixture obtained at the end of the reaction (3), the separation of the 2-(4'-nitrophenyl)-propionic acid (I) is achieved, according to known methods, by acidification, extraction, etc., or, according to a further convenient aspect of this invention, by means of two effective alternative processes, described later on, avoiding the drawbacks of the separation of the solvent, of the phenol, etc. described by the prior art, which uses DMF as a solvent.

By way of illustration, acid (I) is prepared in the following way.

The para-cresol is added to a mixture consisting of: DMSO in a quantity comprised between about 1.5 and 10 mols per mol of para-cresol, but preferably about 2.4 mols, of KOH, in a quantity about equimolar in respect of para-cresol, of water and toluene. This mixture is then heated in a $N_2$ atmosphere until attaining complete distillation of the toluene-water azeotrope; the remaining toluene is then distilled. The remaining solution is then cooled down and $CO_2$ is added at the temperature of 20°–30° C., but preferably at between 25° and 27° C., in order to avoid solidifications, then continued in a stream of $CO_2$ until reaching the end of the absorption. At this point there is gradually added the PNEB, in the desired molar ratio with respect to the potassium para-cresolate, preferably 0.25 mols/mol of para-cresolate, and then, under vigorous stirring, the temperature is brought up to 30°–50° C., preferably to 50° C., maintaining it there for about 3 hours. Higher temperatures may lead to the undesirable formation of salicylic acids.

The mixture thus obtained, containing the potassium salts of the mono- and bi-carboxylic acids, is then treated, according to the known techniques, with mineral acids (HCl, $H_2SO_4$), thermally decarboxylated, extracted, etc.

Or, according to a first effective alternative, the mixture containing the above-mentioned salts is treated with HCl (at 36%) or with $H_3PO_4$ (at 85%) in excess, in order to free the acids, and is then filtered with acetone, then subjected to distillation under vacuum (12–13 mm Hg) in the acid medium, recovering the DMSO and the para-cresol directly in the form of the distillate, while acid (I) is obtained from the residue of the distillation.

The residue is dissolved in toluene or 1,2-dichloroethane and extracted with aqueous NaOH at about 5% concentration, from the aqueous phase; by conventional acidification at 0° C. and at about 1 pH, by precipitation is obtained acid (I).

In a second effective alternative, no distillation or thermal treatment of the reaction mixture is involved. It consists actually in the distribution (or subdivision) of the reaction mixture between a volumetrically reduced aqueous phase and an organic phase chosen from amongst toluene, 1,2-dichloroethane and trichloroethylene. This division (or distribution) is preceded by a treatment with $CO_2$ and water in order to convert the unreacted potassium para-cresolate to para-cresol, while the organic acid remains in the form of an alkaline salt. From the aqueous phase acid (I) is easily recovered from its potassium salt, as indicated above (acidification with HCl, $H_3PO_4$, etc.).

The para-cresol, the unreacted para-nitrobenzene (PNEB) and minor quantities of DMSO are directly recovered from the organic phase.

The remaining greater part of the DMSO is recovered by separate extraction of the aqueous phase wherein it is contained, after the extraction of acid (I). More particularly, the aqueous phase, after concentration, is treated with solid NaOH until obtaining a concentration of about 10%, and then the DMSO is extracted with 1,2-dichloroethane, from the solution of which the DMSO is recovered by distillation and recycled, etc. Alternatively, there may be used n-butanol In both these preferred forms of separation of acid (I) described above, the corresponding organic phases to be recycled, consisting of DMSO and para-cresol, and containing small quantities of unreacted PNEB which, in order to improve the yield and purity of the product, must be separated, before the para-cresol is formed again, by treatment with alkali.

This may be achieved by the addition of aqueous KOH at about 50% concentration, stoichiometrically with reference to the para-cresol to be salified, and by the subsequent extraction of the PNEB from the aqueous solution obtained with toluene. The aqueous solution of the DMSO and of the para-cresolate of K is recycled, etc.

The invention, in comparison to the technique of the most pertinent art, that is with the technique using DMF as the carboxylation solvent, offers advantages of a consistent industrial interest, and more particularly:

(1) it permits the preparation "in situ" of the phenate with all the advantages connected with it, and at the same time to anhydrify the solvent by azeotropic distillation of a mixture of $H_2O$-toluene, and subsequent distillation of toluene;

(2) it permits the recovery of a mixture of DMSO and phenol, in quantities corresponding to 80–90% of the initial quantity, directly usable for a new acid production cycle;

(3) it permits the limitation of environmental safety problems connected with the disposal of the effluents.

Moreover, further advantages connected with the use of DMSO as the solvent associated with potassium para-cresolate as the phenol base, may be seen in the following points: (1) The raw acid is obtained in a very pure state, after separation from the reaction mixture, directly already as a monocarboxylic acid, since there is avoided the decarboxylation (necessary in the DMF process) of the dicarboxylic acid that had formed; (2) The surprising solubility of the potassium p-cresolate in DMSO that allows to operate with DMSO/p-cresolate molar ratios at least halved with respect to the molar ratios DMF/sodium phenate used in the DMF process, and in the presence of a homogeneous solution from the start to the end of the reaction (during the preparation of the potassium para-cresolate in DMSO, treating with $CO_2$ of the same etc.).

DESCRIPTION OF THE SPECIFIC EMBODIMENTS

The invention will now be described in further detail with reference to the following examples, given for simple illustrative purposes, in which is shown a production cycle of acid (I) with the recovery and recycling of the reactants, solvents, etc.

The composition of the distillates and of the aqueous organic phase was determined by gas-chromatography.

EXAMPLE 1

14.6 g (0.1 mol) of potassium p-cresolate were dissolved under stirring in 18 ml of DMSO contained in a 100 ml 4-necked flask, fitted with a stirrer, a coolant and a dropping funnel. The solution was then treated with $CO_2$ under a stream of $CO_2$ at 25° C. until no gas absorption could be observed anymore (less than 1 hour). Thereupon, still under stirring, 3.775 g (0.025 mols) of PNEB were introduced and then the temperature was raised to 50° C. and maintained at this level for 3 hours.

The solution was then allowed to cool down, after which it was poured into iced water (about 100 ml).

Still cooling it, with ice, the solution was then acidified with 10% $H_2SO_4$ up to a pH value of about 1. The acid solution was then extracted with ethyl ether (4 extractions with 50 ml each). The ether extract was shaken three times with $Na_2CO_3$ at 10% concentration, using 40 ml, 30 ml and 30 ml of solution, respectively. The basic aqueous solution was washed twice with 25 ml of ether, then acidified under cold with 10% $H_2SO_4$ to a pH vlaue of about 1. This acid solution was again extracted with ether (4 extractions with 50 ml each). After evaporation of the ether, the residue was heated at 160° C. for 10–15 minutes. Thereby 4.17 g of raw 2-(4'-nitro-phenyl)-propionic acid (titre: 98.43%) were obtained. The yield amounted to 84.19%. This product, examined by thin-layer chromatography (eluent: $CH_2Cl_2/CCl_4/CH_3COOEt/HCOOH = 10/10/5/5$), showed a single spot.

EXAMPLE 2

(Recovery of the Reactants by Distillation)

Into a 4-necked, 500 ml flask fitted with a stirrer and provided with a coolant and dropping funnel, were loaded under a slow $N_2$ stream: 110 g of DMSO; 44.2 g (about 0.41 mols) of p-cresol; 26 g (about 0.40 mols) of an 85% KOH dissolved in 16 ml of water, and 100 ml of toluene. Still under a nitrogen atmosphere, the mixture was heated in a hot oil bath (temperature of the bath: 130°–135° C.) for about 4 hours, until achieving the complete distillation of the water; then there was distilled the toluene (about 95 ml).

In the aqueous fraction (A) (39.7 g) of the distillate (after having shaken the toluene layer with the water itself) there were contained 14.4 g of DMSO (determined by gas-chromatography) which later on were recovered. The solution was then cooled down to 25°–27° C. and treated in a stream of $CO_2$ up to complete absorption (in about 1 hr.).

Under vigorous stirring, 15.1 g (0.1 mol) of PNEB were added as a trickle. The mixture was then slowly heated up to 50° C., whereafter the reaction mixture was kept under stirring at this temperature for 2 hours. Thereupon it was cooled down to room temperature, diluted with 240 of acetone and acidified under cold with 50.8 g of 85% $H_3PO_4$ (0.44 mols; in a 10% excess with reference to the stoichiometric value). The inorganic salt that had formed was then filtered at the water pump, and the cake was then washed twice with, respectively, 70 and 50 ml of acetone, after which it was dried. Thereby were obtained 55.4 g of $KH_2PO_4$.

The filtrate, after distillation of the acetone at atmospheric pressure (290 ml of acetone were recovered) was distilled under vacuum (12–13 mm Hg; bath temperature: 140° C.).

A single fraction was recovered until the heat temperature attained 112°–114° C. The duration of the distillation amounted to about 90 minutes. 133.8 g of the distillate (B) were obtained, containing:

| DMSO | 63.38% | 84.8 g |
| PNEB | 1.60% | 2.14 g |
| p-cresol | 30.92% | 41.37 g | which is recycled, after restoring of the para-cresolate as described further on.

The residue of the distillation was then dissolved in 100 ml of 1,2-dichloroethane and was extracted thrice with NaOH at 50% concentration, using 100 ml, 50 ml and 50 ml, respectively, of the extraction solution.

The aqueous solution was neutralized to a pH=7 with 11 ml of concentrated HCl, and then extracted three times with 30 ml of toluene. The aqueous solution was treated with charcoal, then filtered, stripped and acidified at 0° C. to a pH=about 1, with 15 ml of concentrated HCl. The solution was then allowed to rest at 0° C. for 2–3 hours, whereafter it was filtered and the solid substance thus obtained was washed with cold water and then dried.

Thereby were obtained 16 g of raw 2-(4'-nitro-phenyl)-propionic acid (acidimetric titre: 98.36%). Yield = 80.7%.

Analyzed by thin layer chromatography (eluent: $CH_2Cl_2/CCl_4/CH_3COOEt/HCOOH = 10/10/5/5$), the product showed a single spot.

In the precipitation water (about 230 ml) there were found 2.58 g of DMSO and traces of p-cresol.

Recycle of the DMSO and p-cresol (a) In 40 ml of water (there was included the azeotropic distillation water containing 14.4 g of the DMSO (A) obtained previously) were dissolved 26 grams of 85% KOH.

(b) To the previously obtained distillate (B) (containing 84.8 g of DMSO, 2.14 g of PNEB, 41.37 g of p-cresol) were added 2.8 g of p-cresol and the content of p-cresol was brought back to the initial value (44.2 g).

(c) The two solutions were then combined. The aqueous solution thus obtained was extracted 4 times with 50 ml of toluene. The toluene extracts were then washed with 10 ml of water, which were then admixed to the aqueous fraction. (From the toluene fractions may be recovered the unreacted PNEB).

(d) The aqueous fraction thus obtained was placed into the reactor. To it were then added 10.8 g of fresh DMSO (in order to reach the initial value of 110 g) and 2.2 g of p-cresol. Thereupon were introduced 100 ml of toluene (for this purpose, the toluene of the initial azeotropic distillation was used) and then it was proceeded as above, for a new cycle.

EXAMPLE 3

(Recovery of the Reactants by Stratification)

Into a 500 ml, 4-necked flask, fitted with a stirrer, a coolant and a dropping funnel or tube, there were loaded under moderate $N_2$ flow: 88 g of DMSO, 44.2 g (about 0.41 mols) of p-cresol, 26 g (about 0.40 mols) of 85% KOH dissolved in 16 ml of water, and 100 ml of toluene. Still under a $N_2$-atmosphere, the above mixture was heated for about 4 hours in an oil bath (bath temperature: 130°–135° C.) up to complete distillation of the water; thereupon the toluene (95 ml) was distilled.

In the aqueous fraction (A) of the distillate (after shaking the toluene with the water itself) there were contained 11.05 g of DMSO (determined by gas-chromatography). The solution was then cooled down to 25°–27° C. and treated in a stream of $CO_2$ up to complete absorption (in about 1 hr.). To the solution was then added as a trickle and under vigorous stirring, 15.1 g (0.1 mols) of p-nitroethylbenzene. It was then heated up to 50° C. and the mixture was maintained under stirring at this temperature for 2 hours. Thereupon it was cooled down to room temperature and 20 ml of water were added.

Thereupon the potassium p-cresolate was transformed by a stream of $CO_2$ in p-cresol. The passage of $CO_2$ was maintained until no further absorption could be observed (in about 1 hour).

The mass, containing salts in suspension, was diluted with 250 ml of water added in several portions in order to avoid foaming, thereby obtaining the full solubilization. To this were then added 400 ml of toluene and the mixture was shaken and then allowed to stratify. The layers thus formed were separated and the toluene layer was washed with 10 ml of water.

The toluene layer (B) (406.6 g), analyzed by gas-chromatography, proved to contain:

| DMSO | 2.97% | 12.07 g |
|---|---|---|
| p-cresol | 10.33% | 42.00 g |
| PNEB | 0.37% | 1.50 g | and was then recycled as hereunder described. The aqueous layer, containing the organic salt and the remaining DMSO, was acidified under cold with about 40 ml of concentrated HCl. The solution was then extracted with toluene (3 extractions with 80 ml each). The acid mother liquor (C) (422.5 g) contained 61 g of DMSO (determined by gas-chromatography), recyclable as indicated hereunder. The toluene solution was extracted three times with 5% NaOH using 100 ml, 50 ml and 50 ml, respectively. The toluene was distilled and recovered.

The aqueous alkaline solution was neutralized, under cooling, with 16–17 ml of concentrated HCl, and was then extracted twice with 30 ml of toluene. From the toluene were recovered 2 grams of p-cresol, together with 0.096 g of DMSO.

The aqueous solution was treated with charcoal, filtered, stripped and then acidified at 0° C. with 9 ml of concentrated HCl, until reaching a pH=about 1. The solution was then allowed to rest for 2–3 hours at 0° C., whereafter it was filtered. The solid thus obtained was washed with cold water and finally dried. Thereby were obtained 16.08 g of the raw acid product (I) (acidimetric titre: 98.91%). The yield amounted to 81.56%. Upon thin-layer examination (eluent: $CH_2Cl_2/CCl_4/CH_3COOEt/HCOOH = 10/10/5/5$), the product showed a single spot. In the precipitation water (about 230 ml) there were found 2.95 of DMSO and 0.4 g of p-cresol.

Recycle of the DMSO and p-cresol (I)

(a) The acid mother liquor (C) (422.5 g) containing 61 g of DMSO, was neutralized with NaOH and concentrated by distilling about 180–190 ml of water at atmospheric pressure.

(b) To the remaining aqueous solution were added about 16 g of NaOH tablets. The basic solution thus obtained was extracted in a Soxhlet apparatus with 310 g (250 ml) of 1,2-dichloroethane for about 8 hours. According to the gas-chromatographic examination, in the dichloroethane were found 56.92 g of DMSO. In the residual mother liquor (150 ml) there remained 6 g of DMSO (determined by gas-chromatography), together with about 30 g of KCl.

(c) The dichloroethanic solution was distilled at atmospheric pressure. Thereby were recovered 300 g of 1,2-dichloroethane (containing 1.30 g of DMSO) which were used again in the successive extraction. The distillation was carried on under vacuum (12–13 mm Hg) and there were obtained 59.90 (D) g of DMSO (titre: 97.3%). The extraction yield amounted to 84.75%.

(II)

(a') There were dissolved 26 g of KOH at 85% concentration in 40 ml of water (there was included the water of the azeotropic distillation (A) containing 11.05 g of DMSO;

(b') To the toluene layer (B) (containing 12.07 g of DMSO; 42 g of p-cresol and 1.50 g of PNEB) were added 2.20 g of p-cresol, and the content in p-cresol was thus brought back to the initial value (44.2 g);

(c') The two solutions (a') and (b') were combined, repeatedly shaken and then allowed to stratify. The toluene layer was then washed with 10 ml of water which were added to the aqueous fraction. This aqueous fraction was recycled into the reactor. (From the toluene there may be recovered the unreacted PNEB).

III (a") the distilled DMSO(D) (52.90 g) was added to the aqueous fraction contained in the reactor;

(b") There were then added 13.41 g of fresh DMSO (in order to restore the initial value of 88 g) and 2.2 g of p-cresol;

(c") There were introduced 100 ml of toluene (there was used the toluene of the preceding initial azeotropic distillation) and then it was proceeded to a new cycle, as indicated herein above.

EXAMPLE 4

It was proceeded as in Example 1, using potassium phenate (0.1 mol) in DMSO (35 ml). Thereby was obtained acid (I) with a yield of 85%.

EXAMPLE 5

It was proceeded as in Example 1, using potassium p-(o-tert.-butyl)-cresolate (0.1 mol) in DMSO (35 ml). Thereby was obtained acid (I) with a yield of 86%.

EXAMPLE 6

It was proceeded as in Example 1, using sodium p-(o-tert.-butyl)-cresolate (0.1 mol) in DMSO (50 ml). Thereby was obtained acid (I) with a yield of 85%.

EXAMPLE 7

It was proceeded as in Example 1, using sodium phenate (0.1 mol) in DMSO (35 ml). Thereby was obtained acid (I) with a yield of 65%.

EXAMPLE 8

It was proceeded as in Example 1, using potassium p-cresolate (0.1 mol) in a pyridine-DMSO (27/8 ml) mixture. The reaction temperature was equal to 65° C. while the yield in acid (I) was 66%.

We claim:

1. Process for the preparation of 2-(4'-nitrophenyl)-propionic acid (I) by the carboxylation of para-nitroethylbenzene in a solvent, under substantially atmospheric pressure, and at a temperature of between about 20° and 50° C., in the presence of an alkaline phenate selected from the group consisting of potassium and sodium to form the corresponding potassium or sodium salt of the acid, characterized in that the reaction is conducted in dimethylsulphoxide.

2. Process according to claim 1 which is conducted in the presence of potassium para-cresolate.

3. Process according to claim 1, characterized in that the molar ratio of alkaline phenate: para-nitroethylbenzene is between 1 and 4.

4. Process according to claim 1, characterized in that the separation of acid (I) from its corresponding alkaline salt is obtained by distillation of an acidified aqueous solution of the said salt.

5. Process according to claim 4 wherein the organic residue from said distillation is recycled.

6. Process according to claim 1, characterized in that the separation of acid (I) from its corresponding alkaline salt is obtained by treatment with $H_2O$ and $CO_2$ and by the subsequent subdivision of the reaction mixture with a solvent selected from among toluene, 1,2-dichloroethane and trichloroethylene, from the aqueous phase containing the alkaline salts of acid (I) and the dimethylsulphoxide, the acid (I) being recovered by acidification, and then the dimethylsulphoxide recovered by extraction with a solvent selected from among 1,2-dichloroethane and n-butanol in an alkaline medium, and by a final distillation.

* * * * *